US009073828B2

(12) United States Patent
Kashiwaba et al.

(10) Patent No.: US 9,073,828 B2
(45) Date of Patent: Jul. 7, 2015

(54) PREPARATION METHOD FOR PERFLUOROALKANE SULFINATE

(75) Inventors: Takashi Kashiwaba, Ube (JP);
Tsutomu Nanmyo, Ube (JP); Yoichi Takenaka, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 106 days.

(21) Appl. No.: 13/574,138

(22) PCT Filed: Mar. 3, 2011

(86) PCT No.: PCT/JP2011/054844
§ 371 (c)(1),
(2), (4) Date: Jul. 19, 2012

(87) PCT Pub. No.: WO2011/108622
PCT Pub. Date: Sep. 9, 2011

(65) Prior Publication Data
US 2013/0023695 A1    Jan. 24, 2013

(30) Foreign Application Priority Data

Mar. 4, 2010  (JP) ................................. 2010-047253
Mar. 1, 2011  (JP) ................................. 2011-043594

(51) Int. Cl.
*C07C 313/04*    (2006.01)
(52) U.S. Cl.
CPC .................................. *C07C 313/04* (2013.01)
(58) Field of Classification Search
CPC ............................ C07C 313/04; C07C 313/02
USPC ....................................................... 562/125
See application file for complete search history.

(56) References Cited

U.S. PATENT DOCUMENTS

| 3,919,301 | A | 11/1975 | Roesky et al. |
| 5,565,689 | A | 10/1996 | Clavel et al. |
| 6,462,228 | B1 * | 10/2002 | Dams ........................... 562/125 |
| 6,849,636 | B2 | 2/2005 | Waddell et al. |
| 7,504,402 | B2 | 3/2009 | Waddell et al. |
| 2001/0031891 | A1 | 10/2001 | Goto et al. |
| 2009/0181994 | A1 | 7/2009 | Waddell et al. |

FOREIGN PATENT DOCUMENTS

| JP | 48-56619 B | 8/1973 |
| JP | 9-263548 A | 10/1997 |
| JP | 2001-316353 A | 11/2001 |
| JP | 2005-247782 A | 9/2005 |
| JP | 2006-513266 A | 4/2006 |
| WO | WO 2010/013687 A1 | 2/2010 |

OTHER PUBLICATIONS

Work-up (chemistry) cited reference in 2004.*
PCT/ISA/237 Form (Three (3) pages).
Richard M. Scribner, "Some New Sulfonyl- and Trifluoromethylthio-p-benzoquinones. Their Reactions, Polarographic Reduction Potentials, and π Acid Strengths", J. Org. Chem., Nov. 1966, pp. 3671-3682, vol. 31.
H.W. Roesky et al., "The Chemistry of Trifluorosulfinic Acid and Its Derivatives", Journal of Fluorine Chemistry, 1976, pp. 77-84, vol. 7, No. 77.
R.N. Haszeldine et al., "Perfluoroalkyl Derivatives of Sulphur. Part II.* Trifluoromethane-sulphonic, -sulphinic, and -sulphenic Acid and the Infrared Spectra of Compounds Containing—$SO_2$—and >S:O Groups.", J. Chem. Soc., 1955, pp. 2901-2910.
Bernard R. Langlois et al., "A New Preparation of Trifluoromethanesulfinate Salts", Journal of Fluorine Chemistry, 2007, pp. 851-856, vol. 128.
International Search Report including English language translation dated May 17, 2011 (Four (4) pages).

* cited by examiner

*Primary Examiner* — Yong Chu
(74) *Attorney, Agent, or Firm* — Crowell & Moring LLP

(57) ABSTRACT

In a method for obtaining an alkali metal perfluoroalkanesulfinate by reacting a perfluoroalkanesulfonyl halide with a sulfur-containing reducing agent in the presence of water, a reaction liquid containing the alkali metal sulfinate obtained after the reaction is concentrated till a specific concentration, thereby inorganic salts, which are impurities in the solution, are precipitated and removed, and a filtrate after removing the inorganic salts is subjected to an operation such as concentration and drying, thereby obtaining the target alkali metal perfluorosulfinate with a high purity and a good operability. Furthermore, an organic solvent for extraction becomes unnecessary. Therefore, it is possible to greatly reduce wastes.

6 Claims, No Drawings ical field

The present invention relates to a method for producing a perfluoroalkanesulfinate, which is useful as an organic synthesis intermediate.

BACKGROUND OF THE INVENTION

Perfluoroalkanesulfinates are compounds that are useful, for example, as intermediates of medicine and agricultural chemical raw materials. Patent Publication 1 describes potassium trifluoromethanesulfinate as an intermediate of sulfonyl compounds, which are said to be useful for diabetes, etc. Furthermore, Patent Publication 2 discloses that a perfluoroalkanesulfinate is useful as a perfluoroalkylation agent.

As a conventional method for producing perfluoroalkanesulfinic acid derivatives, there is disclosed in Patent Publication 3 a method for producing a fluoroalkanesulfinic acid by reacting a perfluoroalkanesulfonyl fluoride with hydrazine into a hydrazium salt, and then reacting it with an acid.

Furthermore, Patent Publication 4 discloses a method for producing an alkali metal salt of perfluoroalkanesulfinic acid by bringing a perfluoroalkanesulfonyl fluoride into contact with an alkali metal sulfite in the presence of water. Non-patent Publication 1 discloses a method for obtaining potassium trifluoromethanesulfinate by reacting trifluoromethanesulfonic chloride with potassium sulfite. Non-patent Publication 2 discloses a method of reacting sodium carbonate or potassium carbonate with trifluoromethanesulfinic acid, thereby obtaining a corresponding sulfinate.

Furthermore, Non-patent Publication 3 also discloses that a zinc salt of tifluoromethanesulfinic acid is formed by reacting trifluoromethanesulfonyl chloride with zinc powder.

Furthermore, Non-patent Publication 4 discloses a method for obtaining potassium trifluoromethanesulfinate by reacting benzyl trifluoromethyl sulfone, potassium carbonate, and ethyl 3-bromopropionate.

Furthermore, Patent Publication 5 discloses a method in which hydrazine is reacted on a perfluoroalkanesulfonyl halide to obtain a perfluoroalkanesulfinic acid hydrazine salt ($RfSO_2H.N_2H_4$), followed by a conversion into a perfluoroalkanesulfinate.

PRIOR ART PUBLICATIONS

Patent Publications

Patent Publication 1: Japanese Patent Application Publication 2006-513266.
Patent Publication 2: Japanese Patent Application Publication Heisei 9-263548.
Patent Publication 3: Japanese Patent Application Publication Showa 48-56619.
Patent Publication 4: Japanese Patent Application Publication 2001-316353.
Patent Publication 5: International Publication 2010-013687.

Non-Patent Publications

Non-patent Publication 1: R. M. Scribner, J. Org. Chem., 31, 3671 (1966).
Non-patent Publication 2: H. W. Roesky and G. Holtschneider, J. Fluorine. Chemistry, 7, 77 (1976).
Non-patent Publication 3: R. N. Haszeldine, J. M. Kidd, J. Chem. Soc., 2901-2910 (1955).
Non-patent Publication 4: B. R. Langlois et al, J. Fluorine. Chemistry, 851, 128 (2007).

SUMMARY OF THE INVENTION

The methods of Patent Publication 3 and Non-patent Publication 2 can be named as preferable methods at a glance, since it is possible to obtain the sulfinic acid and the sulfinic acid metal salt with high yields. It is, however, necessary to purify the sulfinic acid by distillation. With this, the sulfinic acid may be decomposed. Furthermore, in a post-treatment procedure, a hazardous substance, hydrazine sulfate, is formed. Therefore, there were some difficulties in producing them with safety and easiness in an industrial scale.

Furthermore, the method of Non-patent Publication 3 is considered to have a danger of explosion in the production in an industrial scale due to the use of metal zinc powder and to have a waste treatment cost due to discharge of zinc-series wastes in large amounts. Therefore, it is difficult to say that the method is a method that is industrially usable.

The method of Non-patent Publication 4 necessitates using an expensive reagent when producing the raw material, benzyl trifluoromethyl sulfone, and is not efficient due to going through a three-step reaction in order to obtain the target product from the starting material. Therefore, it has had some difficulty in terms of production cost.

It is a task of the present invention to provide a method for producing a perfluoroalkane sulfinate in an industrial scale, which is superior in production cost and easiness.

Means for Solving Task

After repeating a further study to solve the task, the present inventors have found, in a method for obtaining an alkali metal perfluoroalkanesulfinate by reacting a perfluoroalkanesulfonyl halide with a sulfur-containing reducing agent in water, that the target product, an alkali metal perfluoroalkanesulfinate, is obtained with high purity and good operability by concentrating a reaction mixture liquid containing the alkali metal sulfinate obtained following the reaction to have a specified concentration, thereby precipitating an inorganic salt, which is an impurity in the solution, then removing it, and then subjecting a filtrate prepared by removing the inorganic salt to an operation such as concentration, drying, etc.

That is, the present invention provides a method for producing an alkali metal perfluoroalkanesulfinate, which is described in the following [Invention 1] to [Invention 5].

[Invention 1]

In a method that a perfluoroalkanesulfonyl halide represented by formula [2]

$$R_fSO_2X \qquad [2]$$

(In the formula, Rf represents a $C_{1-4}$, straight-chain or branched-chain perfluoroalkyl group, and X represents a fluorine, chlorine, bromine or iodine atom.) is reacted with a sulfur-containing reducing agent (Herein, the sulfur-containing reducing agent refers to an alkali metal salt of sulfurous acid, hydrogen sulfite, thiosulfuric acid, dithionous acid, pyrosulfurous acid, or sulfide.) in the presence of water, thereby producing an alkali metal perfluoroalkanesulfinate represented by formula [1]

$$R_fSO_2M \qquad [1]$$

(In the formula, Rf is defined as in formula [2], and M represents lithium, sodium, potassium, rubidium, or cesium.), the method for producing the alkali metal perfluoroalkanesulfinate represented by formula [1] being characterized by that a reaction mixture liquid containing the alkali metal perfluoroalkanesulfinate, which has been obtained following the reaction, is concentrated such that a weight ratio of the alkali metal sulfinate to water becomes 1:2.5 to 1:0.1, and an inorganic salt precipitated after the concentration is separated and removed.

[Invention 2]

The method according to Invention 1, wherein the perfluoroalkanesulfonyl halide represented by formula [2] is a perfluoroalkanesulfonyl chloride or perfluoroalkanesulfonyl fluoride.

[Invention 3]
The method according to Invention 1 or Invention 2, wherein the sulfur-containing reducing agent is sodium sulfite, potassium sulfite, sodium hydrogensulfite, potassium hydrogensulfite, sodium thiosulfate, potassium thiosulfate, or sodium dithionite.

[Invention 4]
The method according to any of Invention 1 to Invention 3, which is characterized by that, when the perfluoroalkanesulfonyl halide represented by formula [2] is reacted with the sulfur-containing reducing agent, a basic compound (herein, the basic compound is a hydroxide, oxide, carbonate or hydrogencarbonate of an alkali metal, and there is used a basic compound having a metal that is identical with that of the alkali metal perfluoroalkanesulfinate represented by formula [1]) is added to the reaction mixture liquid containing the alkali metal perfluoroalkanesulfinate, which has been obtained following the reaction, then pH value of the reaction mixture liquid after the addition is adjusted to 7-9, and then the concentration is conducted.

[Invention 5]
The method according to Invention 4, wherein the basic compound is a hydroxide or carbonate of an alkali metal.

[Invention 6]
The method according to Invention 1 to Invention 5, which is characterized by that water is added to the inorganic salt, which has been separated and removed, to extract the alkali metal perfluoroalkanesulfinate contained in the inorganic salt, and the obtained filtrate containing the alkali metal perfluoroalkanesulfinate is added again to the solution prior to the concentration.

By reacting the perfluoroalkanesulfonyl halide with the sulfur-containing reducing agent in the presence of water, inorganic salts, such as a salt derived from the sulfur-containing reducing agent and a halogen salt, are formed simultaneously with the formation of the target alkali metal perfluoroalkanesulfinate.

It is possible to satisfactorily obtain the target alkali metal sulfinate by conventional methods, for example, Patent Publication 4 and Non-patent Publication 1. However, in order to remove the inorganic salt from the alkali metal sulfinate, it is necessary to remove water from the reaction mixture liquid after the reaction, then extract the target product with an organic solvent, and separate insoluble inorganic salts (In the specification, "separation" refers to an operation to separate solid and liquid, such as filtration or centrifugation.).

Even when the inventors actually conduct a study, the reaction proceeds satisfactorily. However, when removing water from the reaction mixture liquid and then extracting and separating the alkali metal sulfinate with an organic solvent, there has been found a tendency that inorganic salts, such as salt derived from the alkali metal sulfite and halogen salt, are precipitated from the filtrate and that the alkali metal sulfinate obtained following the purification is contaminated with those inorganic salts (see the after-mentioned Comparative Example 1). In this manner, since a part of the inorganic salts, which has been dissolved in the organic solvent, is sometimes precipitated from the filtrate in the separation operation, it has been impossible to efficiently obtain the alkali metal sulfinate with high purity.

In particular, in a study assuming an industrial scale production, inorganic salts have been precipitated from the filtrate during the separation, and furthermore there has been a difficulty in separation of the inorganic salts. Therefore, it has been found that there is a necessity to repeatedly conduct the extraction and separation operations to take a lot of effort and that the amount of the extraction solvent used is large to cause a problem in operability (see the after-mentioned Scheme 1, the left drawing and Comparative Example 2).

Thus, when the present inventors conducted the separation operation after precipitating inorganic salts by concentrating the concentration of the reaction mixture liquid after the reaction to be within a specific range, we have found that there is no salt precipitation from the filtrate after the separation and that separation is also good. Furthermore, since the filtrate is a homogeneous aqueous solution in the present invention, it is easy to check the composition by ion chromatography, etc. In case that inorganic salts have been found in the filtrate, it is possible to precipitate the inorganic salts by concentrating the solvent again. Therefore, according to need, it is possible to obtain the alkali metal perfluoroalkanesulfinate with high purity. Furthermore, there is no need in the present invention to conduct an extraction by organic solvent. As compared with prior art, it is possible to omit operations such as extraction and solvent distillation. Therefore, it has been found to be a useful method that poses fewer burdens on the environment and that can omit the disposal cost (see the right drawing of Scheme 1).

[Scheme 1]

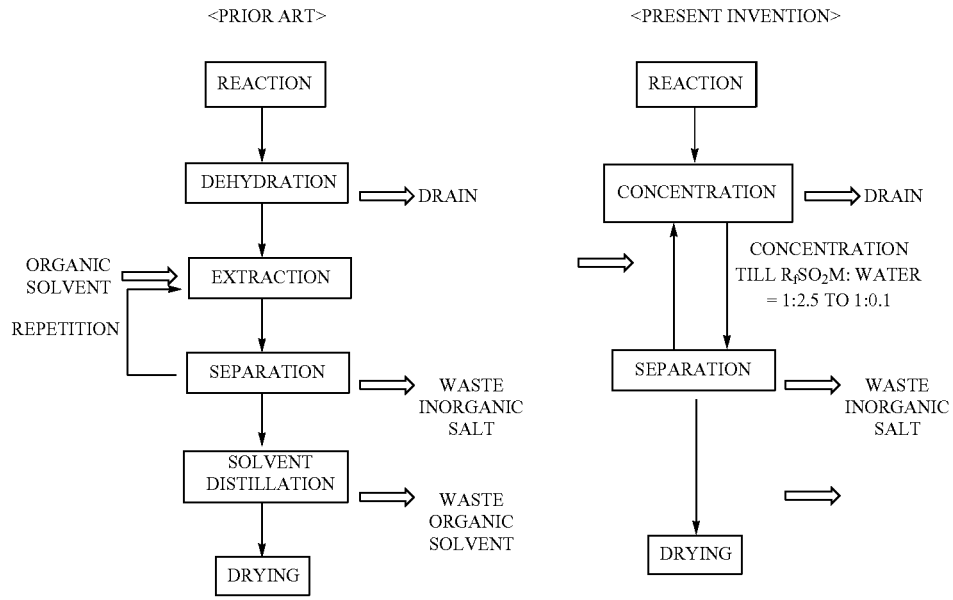

It has been never known that, from a mixed aqueous solution of an organic acid salt and an inorganic salt, the inorganic salt is precipitated, and the organic acid salt is taken out as an aqueous solution, by using operations of concentration and separation as in the present invention.

DETAILED EXPLANATION

It is possible to efficiently produce an alkali metal perfluoroalkanesulfinate with high purity, which is useful as an intermediate of medicines, agricultural chemicals, and functional materials. Furthermore, according to the present invention, an organic solvent for the extraction becomes unnecessary, and it is possible to greatly reduce wastes.

In the following, the present invention is explained in detail. The present invention is a method that a perfluoroalkanesulfonyl halide represented by formula [2] is reacted with a sulfur-containing reducing agent in the presence of water, thereby producing an alkali metal perfluoroalkanesulfinate represented by formula [1], the method for producing the alkali metal perfluoroalkanesulfinate represented by formula [1] being characterized by that a reaction mixture liquid containing the alkali metal perfluoroalkanesulfinate, which has been obtained following the reaction, is concentrated such that a weight ratio of the metal salt to water becomes 1:2.5 to 1:0.1, and an inorganic salt precipitated after the concentration is separated and removed.

The perfluoroalkanesulfonyl halide used in the present invention is represented by formula [2]. Rf is a $C_{1-4}$, straight-chain or branched-chain perfluoroalkyl group, and X is a fluorine, chlorine, bromine or iodine atom. Specifically, it is possible to mention trifluoromethanesulfonyl fluoride, trifluoromethanesulfonyl chloride, trifluoromethanesulfonyl bromide, trifluoromethanesulfonyl iodide, pentafluoroethanesulfonyl fluoride, pentafluoroethanesulfonyl chloride, pentafluoroethanesulfonyl bromide, pentafluoroethanesulfonyl iodide, heptafluoropropanesulfonyl fluoride, heptafluoropropanesulfonyl chloride, heptafluoropropanesulfonyl bromide, heptafluoropropanesulfonyl iodide, nonafluorobutanesulfonyl fluoride, nonafluorobutanesulfonyl chloride, nonafluorobutanesulfonyl bromide, nonafluorobutanesulfonyl iodide, heptafluoropropane-2-sulfonyl fluoride, heptafluoropropane-2-sulfonyl chloride, heptafluoropropane-2-sulfonyl bromide, heptafluoropropane-2-sulfonyl iodide, nonafluorobutane-2-sulfonyl fluoride, nonafluorobutane-2-sulfonyl chloride, nonafluorobutane-2-sulfonyl bromide, nonafluorobutane-2-sulfonyl iodide, hexafluoro-2-trifluoromethyl-propane-1-sulfonyl fluoride, hexafluoro-2-trifluoromethyl-propane-1-sulfonyl chloride, hexafluoro-2-trifluoromethyl-propane-1-sulfonyl bromide, hexafluoro-2-trifluoromethyl-propane-1-sulfonyl iodide, hexafluoro-2-trifluoromethyl-propane-2-sulfonyl fluoride, hexafluoro-2-trifluoromethyl-propane-2-sulfonyl chloride, hexafluoro-2-trifluoromethyl-propane-2-sulfonyl bromide, hexafluoro-2-trifluoromethyl-propane-2-sulfonyl iodide, etc. Preferably, they are trifluoromethanesulfonyl fluoride, trifluoromethanesulfonyl chloride, pentafluoroethanesulfonyl fluoride, pentafluoroethanesulfonyl chloride, heptafluoropropanesulfonyl fluoride, heptafluoropropanesulfonyl chloride, nonafluorobutanesulfonyl fluoride, and nonafluorobutanesulfonyl chloride. Particularly preferably, they are trifluoromethanesulfonyl fluoride and trifluoromethanesulfonyl chloride.

The sulfur-containing reducing agent of the present invention refers to an alkali metal salt of sulfurous acid, hydrogen sulfite, thiosulfuric acid, dithionous acid, pyrosulfurous acid, or sulfide. Specifically, it is possible to mention lithium sulfite, sodium sulfite, potassium sulfite, rubidium sulfite, cesium sulfite, lithium hydrogensulfite, sodium hydrogensulfite, potassium hydrogensulfite, rubidium hydrogensulfite, cesium hydrogensulfite, lithium thiosulfate, sodium thiosulfate, potassium thiosulfate, rubidium thiosulfate, cesium thiosulfate, lithium dithionite, sodium dithionite, potassium dithionite, rubidium dithionite, cesium dithionite, lithium pyrosulfite, sodium pyrosulfite, potassium pyrosulfite, rubidium pyrosulfite, cesium pyrosulfite, lithium sulfide, sodium sulfide, potassium sulfide, rubidium sulfide, cesium sulfide, etc. Above all, sodium sulfite, potassium sulfite, sodium hydrogensulfite, potassium hydrogensulfite, sodium thiosulfate, potassium thiosulfate, and sodium dithionite are particularly preferable.

The usage of the sulfur-containing reducing agent is preferably 1-10 mols, more preferably 1-4 mols, relative to 1 mol of the perfluoroalkanesulfonyl halide.

Normally, the amount of water in the present reaction is preferably 3 g to 100 g, more preferably 3 to 30 g, relative to 1 g of the perfluoroalkanesulfonyl halide used. In case that the amount of water is less than 3 g, the slurry concentration of the reaction liquid is high. Therefore, it is not preferable in terms of operability.

The reaction temperature condition is not particularly limited. It suffices to conduct that in a range of −10° C. to 100° C. Normally, −10° C. to 60° C. is preferable. In particular, 0° C. to 40° C. is more preferable. If the reaction temperature is higher than 100° C., the perfluoroalkanesulfonyl halide is hydrolyzed into an alkali metal perfluoroalkanesulfonate. At a temperature lower than −10° C., the reaction becomes slow. Therefore, it is not preferable.

The perfluoroalkanesulfonyl halide used in the present invention exists, depending on its kind, as liquid or gas under ordinary temperature and ordinary pressure. The condition of the halide upon the feeding is not particularly limited, either gas condition or liquid condition. A person skilled in the art can suitably select the condition of the halide upon the feeding.

The feeding method upon reacting the perfluoroalkanesulfonyl halide with the sulfur-containing reducing agent is not particularly limited. Normally, it can be conducted by adding the perfluoroalkanesulfonyl halide after feeding the sulfur-containing reducing agent into the reactor. For example, as shown in the after-mentioned Examples, in the case of using trifluoromethanesulfonyl fluoride as the perfluoroalkanesulfonyl halide, it is one of particularly preferable modes to previously feed the sulfur-containing reducing agent into the reaction vessel and then add the fluoride at one time, one after another, or continuously, while conducting stirring or pump circulation.

As to a reactor used upon conducting the reaction under pressurized condition, it can be conducted by using a metal container, such as stainless steel, Hastelloy, Monel, etc. Furthermore, in the case of conducting the reaction under ordinary pressure, a person skilled in the art can make a suitable selection in terms of reactor, too.

The pressure during the reaction is normally −0.1 to 10 MPa, preferably −0.1 to 5 MPa, more preferably −0.1 to 2 MPa, in terms of gauge pressure of a pressure gauge attached to the reactor.

The reactor used in the present step is not particularly limited in material, as long as it is pressure-proof upon conducting the reaction under ordinary pressure or increased pressure. It is possible to use a reactor lined with tetrafluoroethylene resin, chlorotrifluoroethylene resin, vinylidene fluoride resin, PFA resin, polypropylene resin, polyethylene resin, glass or the like, or a glass container.

In case that the perfluoroalkanesulfonyl halide exists as gas, it is preferable to conduct that by maintaining the reactor at a low temperature or by using a low-temperature condenser in order that it may not be discharged from the reaction region when introducing it into the reaction system. Furthermore, upon using a normal reactor, it is effective to suitably use a method by a common means for increasing the contact efficiency, such as gas introducing rate adjustment, a stirring device, a gas blowing device, a sparger (a porous sparging tube), etc. Furthermore, it is one of preferable modes to use a scrubber-type reactor using a pump circulation device in order to improve the contact efficiency.

The reaction time is not particularly limited. Normally, it can be conducted in a range of 24 hours or shorter. It is preferable to follow the condition of progress of the reaction by an analysis means, such as ion chromatography, NMR, etc., and judge the time when the raw material substrate has almost disappeared as being the end point.

In the present invention, water is used as solvent. It is possible to use an organic solvent together with water, but it is not particularly preferable since an organic waste liquid is discharged and its disposal requires effort. Normally, it is preferable to conduct the reaction with only water.

Depending on the reagents and conditions used in the reaction, salt may be precipitated upon completion of the reaction. In that case, it is preferable to conduct the next operation after removing the precipitated salt by a normal separation operation.

In the present invention, when the perfluoroalkanesulfonyl halide is reacted with the sulfur-containing reducing agent, the pH value lowers along with the progress of the reaction. By leaving it as it is, the concentration can be conducted, too. It is, however, a preferable method to add a basic compound to the reaction mixture liquid to adjust the pH value and then conduct the concentration operation. As a method of adding the basic compound, it is possible to select either 1) a method of adding after termination of the reaction or 2) a method of adding one after another along with progress of the reaction. In the case of 1), it suffices to adjust the pH value to 7-9 by adding the basic compound in a suitable amount, depending on the pH value after termination of the reaction. In the case of 2), it suffices to conduct an adjustment, in order that the pH value after termination of the reaction may become 7-9, by adding the basic compound while checking the pH value during the reaction. In the case of the method of 2), it is a particularly preferable method, since it is possible to reduce the amount of the sulfur-containing reducing agent, which is necessary for the reaction (see Example 2 and Table 5: It is understood that the sulfur-containing reducing agent used relative to the alkali metal sulfinate obtained in Example 2 has lowered to half of Example 1. However, since the rate of the lowering is not limited to this, but changes depending on the reagents used, it is preferable to examine the condition when it is necessary).

The basic compound of the present invention is a hydroxide, oxide, carbonate or hydrogencarbonate of an alkali metal. Specifically, it is possible to mention lithium hydroxide, sodium hydroxide, potassium hydroxide, rubidium hydroxide, cesium hydroxide, lithium oxide, sodium oxide, potassium oxide, rubidium oxide, cesium oxide (these alkali metal oxides are hydroxides in the presence of water), lithium carbonate, sodium carbonate, potassium carbonate, rubidium carbonate, cesium carbonate, lithium hydrogencarbonate, sodium hydrogencarbonate, potassium hydrogencarbonate, rubidium hydrogencarbonate, cesium hydrogencarbonate, etc., and there is used a metal that is identical with that of the sulfur-containing reducing agent. For example, in the case of using potassium sulfite as the sulfur-containing reducing agent, it is necessary to provide a compound having potassium as a counter cation of the basic compound. Specifically, potassium hydroxide, potassium oxide, potassium carbonate, etc. are preferable, and potassium hydroxide and potassium carbonate are particularly preferable.

By conducting the pH adjustment with the basic compound, a salt may be precipitated depending on the reagent. In that case, it is preferable to conduct the next operation after removing the precipitated salt by a normal separation operation.

Then, a post-treatment after the reaction, which is a characteristic of the present invention, is explained in detail.

It suffices to conduct the concentration of the reaction liquid by a normal distillation operation, such as distillation under reduced pressure. It suffices to conduct the concentration such that the weight of water becomes 0.1 to 2.5 parts, preferably 0.1 to 1.5 parts, particularly preferably 0.1 to 1.0 part, provided that the weight of the alkali metal perfluoroalkanesulfinate in the solution is 1 part. In case that the proportion of water is higher than 2.5, the precipitation of inorganic salts, particularly halides, in the reaction liquid is insufficient. In contrast, if the proportion of water is smaller than 0.1, the target alkali metal perfluoroalkanesulfinate is also precipitated together with inorganic salts to lower yield. Therefore, it is not preferable (see Comparative Example 2). The concentration of water may be conducted several times in parts until the target weight ratio. It is preferable to separate and remove the precipitated inorganic salts each time in terms of operability.

Normally, a solid is precipitated from the reaction liquid after the concentration by concentrating water, irrespective of temperature. The temperature and the time necessary for the precipitation are different depending on the types of inorganic salts contained in the reaction liquid and on the degree of the concentration. Therefore, it is preferable to suitably change the conditions.

It suffices to conduct a normal separation operation on the precipitated inorganic salts. The operation temperature at that time is normally around −10 to 100° C., preferably −10 to 70° C., particularly preferably 0 to 50° C.

The salt separated and removed may contain the target alkali metal perfluoroalkanesulfinate. In that case, it is possible to extract the target alkali metal sulfinate by adding water to this inorganic salt and then stirring for about 1 hour. It is possible to recover the target alkali metal sulfinate by adding the filtrate obtained by the extraction to the mixed liquid prior to the repetitive concentration or to the mixed liquid, prior to the concentration, of another batch reaction, thereby improving the productivity and making waste reduction possible. Therefore, it is one of preferable modes (see Scheme 2).

[Scheme 2]

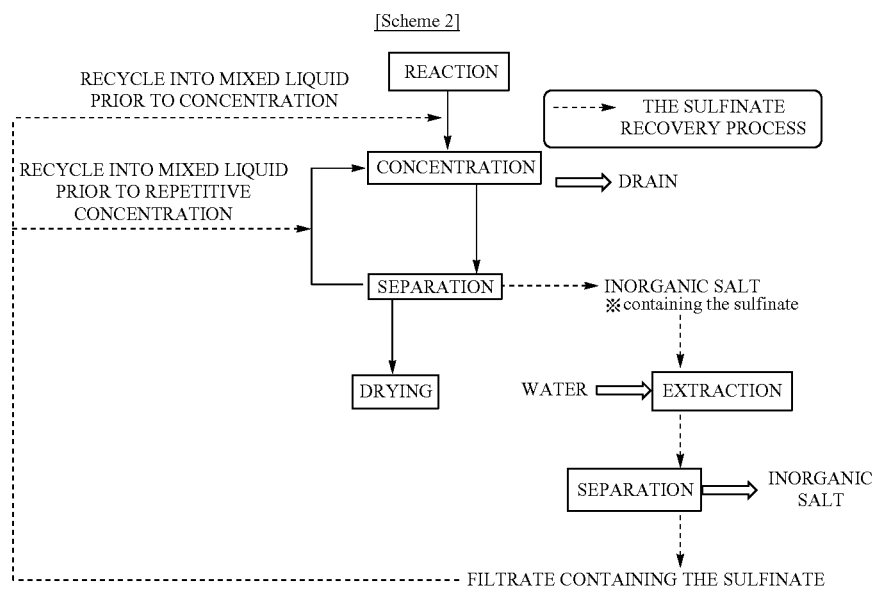

By conducting the measurement, such as ion chromatography, on the filtrate obtained by the separation, its composition can be checked. In case that unnecessary inorganic salts remain, it is possible to remove the inorganic salts by conducting again the concentration in the same range as above. By subjecting the filtrate, from which inorganic salts have sufficiently been removed, to the water removal and drying by a normal operation, such as distillation under reduced pressure, it is possible to obtain the target alkali metal perfluoroalkanesulfinate with a high purity. Alternatively, water may be removed by adding an organic solvent, such as toluene, to the filtrate and then an azeotropic water removal. The conditions upon the water removal and the drying are not particularly limited. It may be conducted at an operation temperature normally in a range of 20 to 120° C., preferably 20 to 100° C., particularly preferably 40 to 80° C.

Furthermore, it is also possible to extract the alkali metal perfluoroalkanesulfinate by adding an organic solvent, such as acetone, acetonitrile, ethyl acetate, methanol, ethanol, etc., to the solid after the drying. It is, however, not particularly preferable, since it takes a lot of trouble with dumping by using an organic solvent.

EXAMPLES

In the following, the present invention is explained in detail by examples. The present invention is not limited to these examples. Herein, "%" of the composition analysis value represents "wt %" of a composition obtained by directly measuring the reaction liquid with ion chromatography.

Example 1

A Reaction Using Trifluoromethanesulfonyl Chloride and Potassium Sulfite

Concentration Until the Alkali Metal Sulfinate Water=1:0.37 by Weight Ratio

A 500 ml, four-necked flask was charged with 250 g of water and 150 g (0.945 mol) of potassium sulfite, followed by cooling the solution. When it became 5° C. or lower, 53.0 g (0.315 mol) of trifluoromethanesulfonyl chloride was slowly added by using a dropping funnel, while maintaining an inside temperature of 5 to 10° C. After the dropping of the trifluoromethanesulfonyl chloride terminated, it was continued to stir the reaction liquid as it was. 12 hours later, the reaction liquid was filtered under 0° C. to remove inorganic salts undissolved. Then, pH of the reaction liquid was checked, and pH was adjusted to about 9 by adding 47 g of 48% KOH aqueous solution. At this time an inorganic salt, such as potassium sulfate, was precipitated, and therefore this was removed by filtration under 0° C. Water was distilled out of the obtained filtrate under reduced pressure to remove 194 g of water. This solution was cooled down until 0° C. to precipitate solid. The solid was removed by filtration. Water was distilled out of the obtained filtrate under reduced pressure to remove 40 g of water. This solution was cooled down until 0° C. to precipitate solid. The solid was removed by filtration. In 56 g of the obtained filtrate, 40 g of potassium trifluoromethanesulfinate and 15 g of water were contained, and the ratio was 1:0.37. The obtained filtrate was concentrated and dried under reduced pressure, thereby obtaining 41.8 g of potassium trifluoromethanesulfinate (yield: 77%) with a purity of 96.7% (the analysis result of ion chromatography) (the composition is shown in Table 1). Of waste materials generated at this time, solid matter (inorganic salts and organic acid salts) weighed 201 g, and waste water weighed 249.1 g. There was no organic waste liquid.

[Recovery Process]

As a result of analyzing 201 g of the solid waste material generated by ion chromatography, potassium trifluoromethanesulfinate was contained by 4.1 g in this inorganic salt. 200 g of water was added to this, followed by stirring for 1 hour and then filtration. With this, the obtained filtrate contained 3.5 g of potassium trifluoromethanesulfinate. Therefore, it was possible to recover 86% of potassium trifluoromethanesulfinate from the inorganic salt.

TABLE I

| | Example 1 | |
|---|---|---|
| Component | CF3SO2K | Inorganic salts in total |
| Content (wt %) | 96.7 | 2.14 |

Example 2

A Reaction Using Trifluoromethanesulfonyl Chloride and Potassium Sulfite while Conducting pH Adjustment as Occasion Arises Concentration Until the Alkali Metal Sulfinate:Water=1:0.42 by Weight Ratio A 300 ml, four-necked flask was charged with 100 g of water and 71.2 g (0.450 mol) of potassium sulfite, followed by cooling the solution. When it became 5° C. or lower, 50.6 g (0.300 mol) of trifluoromethanesulfonyl chloride was slowly added by using a dropping funnel, while maintaining an inside temperature of 5 to 10° C. At this time, pH of the reaction solution was timely checked. When pH was acidic, the pH value was adjusted to about 7 by adding 48% KOH aqueous solution (the total amount of 48% KOH aqueous solution added: 62.9 g). After the dropping of the trifluoromethanesulfonyl chloride terminated, it was continued to stir the reaction liquid as it was. 12 hours later, an inorganic salt, such as potassium sulfate, was precipitated by cooling the reaction liquid till 0° C. Therefore, this was removed by filtration. Water was distilled out of the obtained filtrate under reduced pressure to remove 98.6 g of water. This solution was cooled down until 0° C. to precipitate solid. The solid was removed by filtration. Water was again distilled out of the obtained filtrate under reduced pressure to remove 12.8 g of water. This solution was cooled down until 0° C. to precipitate solid. The solid was removed by filtration. In 57 g of the obtained filtrate, 39 g of potassium trifluoromethanesulfinate and 16.4 g of water were contained, and the ratio was 1:0.42. The obtained filtrate was concentrated and dried under reduced pressure, thereby obtaining 40.6 g of potassium trifluoromethanesulfinate (yield: 78.6%) with a purity of 96.1% (the analysis result of ion chromatography) (the composition is shown in Table 2). Of waste materials generated at this time, solid matter weighed 102 g, and waste water weighed 122 g. There was no organic waste liquid.

[Recovery Process]

As a result of analyzing 102 g of the solid waste material generated by ion chromatography, potassium trifluoromethanesulfinate was contained by 3.0 g in this inorganic salt. 100 g of water was added to this, followed by stirring for 1 hour and then filtration. With this, the obtained filtrate contained 2.7 g of potassium trifluoromethanesulfinate. Therefore, it was possible to recover 90% of potassium trifluoromethanesulfinate from the inorganic salt.

TABLE 2

| | Example 2 | |
|---|---|---|
| Component | CF3SO2K | Inorganic salts in total |
| Content (wt %) | 96.1 | 2.33 |

Comparative Example 1

A Reaction Using Trifluoromethanesulfonyl Chloride and Potassium Sulfite

Water is Removed from the Reaction Liquid, Followed by Extraction with Methanol and then Separation and Drying A 500 ml, four-necked flask was charged with 250 g of water and 150 g (0.945 mol) of potassium sulfite, followed by cooling the solution. When it became 5° C. or lower, 53.0 g (0.315 mol) of trifluoromethanesulfonyl chloride was slowly added by using a dropping funnel, while maintaining an inside temperature of 5 to 10° C. When the dropping of the trifluoromethanesulfonyl chloride terminated, it was continued to stir the reaction liquid as it was. 12 hours later, the reaction liquid was cooled till 0° C., followed by filtration to remove undissolved inorganic salts. Then, pH of the reaction liquid was checked, and pH was adjusted to about 9 by adding 42 g of 48% KOH aqueous solution. Water was removed from the obtained solution under reduced pressure. To the obtained solid matter, 140 g of methanol was added to extract potassium trifluoromethanesulfinate, and inorganic salts undissolved in the solvent were removed by filtration. Although inorganic salts were precipitated from the obtained filtrate, separation was difficult. Therefore, the filtrate was concentrated and dried as it was under reduced pressure, thereby obtaining 40.5 g of potassium trifluoromethanesulfinate (yield: 75%) with a purity of 95.6% (the analysis result of ion chromatography) (composition is shown in Table 3). Of waste materials generated at this time, solid matter weighed 186 g, waste water weighed 260.3 g, and organic waste liquid weighed 135 g.

TABLE 3

| | Comparative Example 1 | |
|---|---|---|
| Component | CF3SO2K | Inorganic salts in total |
| Content (wt %) | 95.6 | 4.26 |

Comparative Example 2

A Large-Scale Reaction Using Trifluoromethanesulfonyl Chloride and Potassium Sulfite Water is Removed from the Reaction Liquid, Followed by Extraction with Methanol and then Separation and Drying A 1000 L SUS reactor was charged with 450 kg of water and 288 kg (1.82 kmol) of potassium sulfite, followed by cooling the solution. When the inside temperature became 5° C. or lower, 100 kg (0.593 kmol) of trifluoromethanesulfonyl chloride was slowly added to maintain an inside temperature of 5 to 10° C. When the dropping of the trifluoromethanesulfonyl chloride terminated, it was continued to stir the reaction liquid as it was. 12 hours later, the reaction liquid was cooled till 3° C. to remove undissolved inorganic salts by filtration. Then, pH of the reaction liquid was checked, and pH was adjusted to about 9 by adding 100 kg of 40% KOH aqueous solution. From the obtained solution, 500 kg of water was removed under reduced pressure. Then, 500 kg of toluene was added, and the solution was distilled again under reduced pressure to remove 35 kg of water. After the concentration, solid matter precipitated in the solution was taken by a centrifugal separator. To the obtained solid matter, 198 kg of methanol was added to extract potassium trifluoromethanesulfinate, and inorganic salts undissolved in solvent were removed by filtration. In the inorganic salts, however, potassium trifluoromethanesulfinate still existed. Therefore, an extraction operation was further conducted two times with 132 kg of methanol. However, when the obtained solution was allowed to stand still, an inorganic salt was precipitated. It was difficult to separate this inorganic salt by a filtration operation. Therefore, only the supernatant of the methanol solution was taken, and solid matter was removed. The obtained supernatant was concentrated. Finally, 106 kg of toluene was added, followed by azeotropic dehydration drying to obtain 62.3 kg (yield 64%) of potassium trifluoromethanesulfinate with a purity of 95% (the analysis result of ion chromatography) (composition is shown in Table 4). Of waste materials generated at this time, solid matter weighed 369 kg, waste water weighed 535 kg, organic waste liquid necessary for the extraction weighed 485 kg, and the total of the waste organic liquid weighed 1012 kg.

TABLE 4

Comparative Example 2

| Component | CF3SO2K | Inorganic salts in total |
|---|---|---|
| Content (wt %) | 95.1 | 4.50 |

Thus, there becomes necessary an organic waste liquid treatment when water is removed from the reaction liquid, followed by conducting an extraction and separation operation with an organic solvent. In a large-scale as in Comparative Example 2, there is discharged an organic waste liquid derived from the extraction, which is 7.8 times the target potassium trifluoromethanesulfinate. Therefore, the disposal cost increases. As compared with those, in the present invention, an organic solvent for the extraction is unnecessary. Therefore, it is considered to be advantageous in terms of cost. Furthermore, when pH value after the termination of the reaction is adjusted to 7-9 by conducting a pH adjustment at a suitable timing while checking pH value during the reaction like Example 2, the reduction of waste water and waste inorganic salts becomes possible along with the reduction of potassium sulfite to be used (see Table 5).

TABLE 5

| | CF3SO2K yield (g) | Potassium sulfite usage (g) | Waste water (g) | Waste solid matter (g) | Organic waste liquid (g) |
|---|---|---|---|---|---|
| Example 1 | 41.8 | 150 | 249 | 201 | — |
| Example 2 | 40.6 | 71.2 | 122 | 102 | — |
| Com. Ex. 1 | 40.5 | 150 | 260 | 186 | 135 |
| Com. Ex. 2 | 62.3 kg | 288 kg | 535 kg | 369 kg | 1012 kg 485 kg* |

*derived from extraction solvent

Example 3

A Reaction Using Trifluoromethanesulfonyl Fluoride and Potassium Sulfite

Concentration Until the Alkali Metal Sulfinate Water=1:0.39 by Weight Ratio

A 500 mL, autoclave reactor was charged with 250 g of water and 150 g (0.945 mol) of potassium sulfite, followed by cooling the solution. When it became 5° C. or lower, the inside of the reactor was deaerated. After the deaeration, 48.0 g (0.316 mol) of trifluoromethanesulfonyl fluoride gasified was slowly introduced, while maintaining an inside temperature of 5 to 10° C. After the introduction of the trifluoromethanesulfonyl fluoride terminated, stirring was continued for 13 hours as it was. 13 hours later, the inside of the reactor was replaced with nitrogen, followed by taking the reaction liquid out. The reaction liquid was cooled till 0° C., and the precipitated inorganic salts such as potassium sulfate were removed by filtration. After checking pH of the reaction liquid, 52 g of 48% KOH aqueous solution was added such that pH became about 9. Since an inorganic salt was then precipitated, this was removed by filtration under 0°. Water was distilled out of the obtained filtrate under reduced pressure to remove 177 g of water. This solution was cooled down until 0° C. to precipitate solid. The solid was removed by filtration. Water was distilled out of the obtained filtrate under reduced pressure to remove 36 g of water. This solution was cooled down until 0° C. to precipitate solid. The solid was removed by filtration. In 59 g of the obtained filtrate, 41.5 g of potassium trifluoromethanesulfinate and 16.6 g of water were contained, and the ratio was 1:0.39. The obtained filtrate was concentrated and dried under reduced pressure, thereby obtaining 42.8 g of potassium trifluoromethanesulfinate (yield: 79%) with a purity of 96.9% (the analysis result of ion chromatography) (composition is shown in Table 6). Of waste materials generated at this time, solid matter weighed 201.4 g, and waste water weighed 229.4 g. There was no organic waste liquid.

TABLE 6

Example 3

| Component | CF3SO2K | Inorganic salts in total |
|---|---|---|
| Content (wt %) | 96.9 | 2.00 |

Example 4

A Reaction Using Trifluoromethanesulfonyl Chloride and Sodium Thiosulfate

Concentration Until the Alkali Metal Sulfinate Water=1:0.43 by Weight Ratio

A 500 ml, four-necked flask was charged with 250 g of water and 149.4 g (0.945 mol) of sodium thiosulfate, followed by cooling the solution. When it became 5° C. or lower, 53 g (0.315 mol) of trifluoromethanesulfonyl chloride was slowly added by using a dropping funnel, while maintaining an inside temperature of 5 to 10° C. After the dropping of the trifluoromethanesulfonyl chloride terminated, it was continued to stir the reaction liquid as it was. 15 hours later, the reaction liquid was filtered under 0° C. to remove inorganic salts undissolved. Then, pH of the reaction liquid was checked, and 73.7 g of 30% NaOH aqueous solution was added such that pH became about 9. At this time an inorganic salt was precipitated, and therefore this was removed by cooling till 0° C. and filtration. The obtained filtrate was distilled under reduced pressure to remove 165 g of water. This solution was cooled down until 0° C. to precipitate solid. The solid was removed by filtration. The obtained filtrate was distilled under reduced pressure to remove 30 g of water. This solution was cooled down until 0° C. to precipitate solid. The solid was removed by filtration. In 54 g of the obtained filtrate, 36.8 g of sodium trifluoromethanesulfinate and 16 g of water were contained, and the ratio was 1:0.43. The obtained filtrate was concentrated and dried under reduced pressure, thereby obtaining 38.3 g of sodium trifluoromethanesulfinate (yield: 78%) with a purity of 96.5% (the analysis result of ion chromatography) (composition is shown in Table 7). Of waste materials generated at this time, solid matter weighed 158 g, and waste water weighed 211 g. There was no organic waste liquid.

TABLE 7

| | Example 4 | |
|---|---|---|
| Component | CF3SO2K | Inorganic salts in total |
| Content (wt %) | 96.5 | 2.44 |

Example 5

A Reaction Using Trifluoromethanesulfonyl Chloride and Sodium Sulfite

Concentration Until the Alkali Metal Sulfinate:Water=1:0.2 by Weight Ratio

A 500 ml, four-necked flask was charged with 250 g of water and 119 g (0.945 mol) of sodium sulfite, followed by cooling the solution. When it became 5° C. or lower, 53.0 g (0.315 mol) of trifluoromethanesulfonyl chloride was slowly added by using a dropping funnel, while maintaining an inside temperature of 5 to 10° C. After the dropping of the trifluoromethanesulfonyl chloride terminated, it was continued to stir the reaction liquid as it was. 12 hours later, the reaction liquid was filtered to remove inorganic salts undissolved. Then, pH of the reaction liquid was checked, and 73.7 g of 30% NaOH aqueous solution was added such that pH became about 9. An inorganic salt was precipitated, and therefore this was removed by filtration. Water was distilled out of the obtained filtrate under reduced pressure to remove 179 g of water. This solution was cooled down until 0° C. to precipitate solid. The solid was removed by filtration. Water was distilled out of the obtained filtrate under reduced pressure to remove 40 g of water. This solution was cooled down until 0° C. to precipitate solid. The solid was removed by filtration. In 37 g of the obtained filtrate, 32 g of sodium trifluoromethanesulfinate and 5.2 g of water were contained, and the ratio was 1:0.2. The obtained filtrate was concentrated and dried under reduced pressure, thereby obtaining 32.3 g of sodium trifluoromethanesulfinate (yield: 65.1%) with a purity of 99.1% (the analysis result of ion chromatography) (composition is shown in Table 8).

Example 6

A Reaction Using Trifluoromethanesulfonyl Chloride and Sodium Sulfite

Concentration Until the Alkali Metal Sulfinate:Water=1:0.9 by Weight Ratio

Using 250 g of water, 150 g of sodium sulfite and 53 g of trifluoromethanesulfonyl chloride, the reaction and the pH adjustment were conducted by the same operation as that of Example 1, following by concentration until the weight ratio of the alkali metal sulfinate to water became 1:0.9. In the same manner as that of Example 1, filtration and drying were conducted, thereby obtaining 39.3 g of sodium trifluoromethanesulfinate (yield: 71.5%) with a purity of 89.5% (composition is shown in Table 8).

Example 7

A Reaction Using Trifluoromethanesulfonyl Chloride and Sodium Sulfite

Concentration Until the Alkali Metal Sulfinate:Water=1:1.2 by Weight Ratio

Using 250 g of water, 150 g of sodium sulfite and 53 g of trifluoromethanesulfonyl chloride, the reaction and the pH adjustment were conducted by the same operation as that of Example 1, following by concentration until the weight ratio of the alkali metal sulfinate to water became 1:1.2. In the same manner as that of Example 1, filtration and drying were conducted, thereby obtaining 44.6 g of sodium trifluoromethanesulfinate (yield: 76.8%) with a purity of 84.6% (composition is shown in Table 8).

Comparative Example 3

A Reaction Using Trifluoromethanesulfonyl Chloride and Sodium Sulfite

Concentration Until the Alkali Metal Sulfinate:Water=1:3.0 by Weight Ratio

Using 250 g of water, 150 g of sodium sulfite and 53 g of trifluoromethanesulfonyl chloride, the reaction and the pH adjustment were conducted by the same operation as that of Example 1, following by concentration until the weight ratio of the alkali metal sulfinate to water became 1:3.0. In the same manner as that of Example 1, filtration and drying were conducted, thereby obtaining 67.8 g of sodium trifluoromethanesulfinate (yield: 83.6%) with a purity of 60.6% (composition is shown in Table 8).

Thus, in case that the degree of concentration is insufficient and thereby the weight ratio of the alkali metal sulfinate:water is lower than the range of the present invention, the removal of inorganic salts (mainly halogen salts) is insufficient and thereby purity of the target alkali metal trifluoromethanesulfinate becomes low. (see Table 8)

TABLE 8

| | Conc. (wt. ratio) Alkali metal sulfinate:water | Composition (g) | | | Purity (wt %) |
| --- | --- | --- | --- | --- | --- |
| | | CF3SO2Na | CP3SO3Na | Inorganic salts (amount of NaCl therein) | |
| Example 5 | 1:0.2 | 32.0 | 0.06 | 0.24 (0.08) | 99.1 |
| Example 6 | 1:0.9 | 35.7 | 0.11 | 4.09 (2.89) | 89.5 |
| Example 7 | 1:1.2 | 37.8 | 0.07 | 6.81 (5.45) | 84.6 |
| Com. Ex. 3 | 1:3.0 | 41.1 | 1.87 | 24.9 (19.7) | 60.6 |

Examples 5-7 and Comparative Example 3

The invention claimed is:

1. A method for producing a mixture liquid containing an alkali metal perfluoroalkanesulfinate represented by formula [1]

$$R_fSO_2M \quad [1]$$

wherein $R_f$ represents a $C_{1-4}$, straight-chain or branched-chain perfluoroalkyl group, and M represents lithium, sodium, potassium, rubidium, or cesium, the method comprising the steps of:

(a) reacting a perfluoroalkanesulfonyl halide represented by formula [2]

$$R_fSO_2X \quad [2]$$

wherein $R_f$ is defined as in formula [1], and X represents a fluorine, chlorine, bromine or iodine atom, with a sulfur-containing reducing agent that is an alkali metal salt of sulfurous acid, hydrogen sulfite, thiosulfuric acid, dithionous acid, pyrosulfurous acid, or sulfide, in the presence of water, the alkali metal salt containing an alkali metal corresponding to M in formula [1], thereby producing a reaction mixture liquid containing the alkali metal perfluoroalkanesulfinate represented by formula [1];

(b) concentrating the reaction mixture liquid containing the alkali metal perfluoroalkanesulfinate, which has been obtained by step (a), such that a weight ratio of the alkali metal perfluoroalkanesulfinate to water becomes 1:2.5 to 1:0.1; and (c) separating an inorganic salt precipitated in the reaction mixture liquid after the concentration in step (b), from the reaction mixture liquid.

2. The method according to claim 1, wherein the perfluoroalkanesulfonyl halide represented by formula [2] is a perfluoroalkanesulfonyl chloride or perfluoroalkanesulfonyl fluoride.

3. The method according to claim 1, wherein the sulfur-containing reducing agent is sodium sulfite, potassium sulfite, sodium hydrogensulfite, potassium hydrogensulfite, sodium thiosulfate, potassium thiosulfate, or sodium dithionite.

4. The method according to claim 1, wherein a basic compound that is a hydroxide, oxide, carbonate or hydrogencarbonate of an alkali metal, and contains a metal that is identical with that of the alkali metal perfluoroalkanesulfinate represented by formula [1], is added to the reaction mixture liquid containing the alkali metal perfluoroalkanesulfinate, which has been obtained following the reaction of step (a), thereby adjusting the pH value of the reaction mixture liquid to 7-9 after the addition, and then the concentration of step (b) is conducted.

5. The method according to claim 4, wherein the basic compound is a hydroxide or carbonate of an alkali metal.

6. The method according to claim 1, wherein water is added to the inorganic salt, which has been separated by step (c), to extract the alkali metal perfluoroalkanesulfinate contained in the inorganic salt, and the obtained filtrate containing the alkali metal perfluoroalkanesulfinate is added again to the solution prior to the concentration of step (b).

* * * * *